United States Patent
Metten et al.

(10) Patent No.: US 9,918,917 B2
(45) Date of Patent: Mar. 20, 2018

(54) STYLING AGENTS HAVING A HIGH DEGREE OF CURL RETENTION

(71) Applicant: Henkel AG & Co. KGaA, Duesseldorf (DE)

(72) Inventors: Diane Metten, Hamburg (DE); Julia Bibiane Lange, Sievershuetten (DE); Bernd Richters, Hamburg (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 15/163,062

(22) Filed: May 24, 2016

(65) Prior Publication Data

US 2016/0262998 A1    Sep. 15, 2016

Related U.S. Application Data

(63) Continuation of application No. PCT/DE2014/200533, filed on Oct. 6, 2014.

(30) Foreign Application Priority Data

Dec. 4, 2013 (DE) .......... 10 2013 224 868

(51) Int. Cl.
| | | |
|---|---|---|
| *A61K 8/39* | (2006.01) | |
| *A61K 8/37* | (2006.01) | |
| *A61Q 5/04* | (2006.01) | |
| *A61Q 5/06* | (2006.01) | |
| *A61K 8/04* | (2006.01) | |
| *A61K 8/81* | (2006.01) | |
| *B65D 83/14* | (2006.01) | |

(52) U.S. Cl.
CPC ............ *A61K 8/39* (2013.01); *A61K 8/046* (2013.01); *A61K 8/375* (2013.01); *A61K 8/8158* (2013.01); *A61Q 5/04* (2013.01); *A61Q 5/06* (2013.01); *B65D 83/752* (2013.01)

(58) Field of Classification Search
None
See application file for complete search history.

(56) References Cited

U.S. PATENT DOCUMENTS 6,503,479 B1 * 1/2003 LesAulnier ............ A61K 8/046
424/45

FOREIGN PATENT DOCUMENTS

| DE | 102010048056 A1 | 4/2012 | |
|---|---|---|---|
| JP | 2007-031378 | * 2/2007 | ............ A61K 8/37 |
| WO | 2010/019766 A1 | 2/2010 | |
| WO | 2011/077083 A1 | 6/2011 | |
| WO | 2012/054029 A1 | 4/2012 | |
| WO | 2013/019969 A2 | 2/2013 | |

OTHER PUBLICATIONS

Gao et al., J. Cosmet. Sci., 2009, vol. 60, pp. 187-197.*
PCT International Search Report (PCT/DE2014/200533) dated Dec. 19, 2014.

* cited by examiner

*Primary Examiner* — Brian Gulledge
(74) *Attorney, Agent, or Firm* — P. Scott Smith

(57) ABSTRACT

The invention relates to styling agents, comprising—with respect to the weight thereof—0.1 to 20 wt % of strengthening polymer(s) and 0.1 to 5 wt % of esters of the formula (I), in which R1 stands for —H or $CH_3$, R2 stands for a straight-chain or branched alkyl group having 7 to 15 carbon atoms, and n stands for an integer from the group 1, 2, 3, 4, 5, 6, 7, 8. Said styling agents effect significantly improved curl retention, in particular significantly improved high-humidity curl retention, thus a higher degree of curl retention even in a humid environment in addition to further improved hold and improved hair feel, such as texture and combability.

12 Claims, No Drawings

STYLING AGENTS HAVING A HIGH DEGREE OF CURL RETENTION

FIELD OF THE INVENTION

The present invention generally relates to styling agents based on a specific combination of polymer(s) and particular esters, to the use of said cosmetic agents for temporarily shaping keratin fibers, and to cosmetic methods using said agents.

BACKGROUND OF THE INVENTION

Polymers are widely used in a large variety of cosmetic agents. They are found in skin treatment agents, in hair treatment agents, in agents that can be washed off or out again immediately after use ("rinse-off" products), and in agents that remain on the skin or hair ("leave-on" agents). In the process, the polymers are used for many different reasons and specific properties of the polymers are taken advantage of in each case. In skin treatment agents, shampoos, conditioners and hair masques, the most important properties of the polymers are often the thickening or nourishing properties. In agents for temporarily shaping keratin fibers, also referred to in the following as styling agents, film-forming and/or stabilizing effects are in particular desired alongside the above properties. Polymers are often used as auxiliary agents to improve, or even enable, the deposition and setting of other active substances and ingredients on the skin or the hair. In this way, by adding appropriate polymers to hair dyes for example, the rubfastness and durability of the dying can be increased.

Generally, cosmetic agents include individual polymers that are specially designed to achieve a very specific effect. If various effects are desired, multiple polymers have to be added. If too many different polymers are used, however, this may produce a number of drawbacks. Problems can occur for example during the formulation, for example because the polymers react with one another or with other constituents of the agent and may precipitate out or break down. Some polymers have a tendency to be deposited on the skin, and in particular on the hair, in such a resistant manner that they can no longer be completely removed with a normal wash, and the polymer accumulates in an undesirable manner and the skin or hair thus ultimately becomes loaded therewith.

Consequently, there is a constant need for polymers or suitable combinations of a small number of polymers that exhibit as many of the desired properties as possible at the same time.

In the case of the styling agents, for example, the polymers used have to provide the hair being treated with as strong a hold as possible. In addition to a high degree of hold, however, styling agents have to satisfy a whole array of other requirements. These can be roughly grouped into properties on the hair, properties of the formulation in each case, e.g. properties of the mousse, the gel or the sprayed aerosol, and properties relating to the handling of the styling agent, with the properties on the hair being particularly important. These include in particular resistance to moisture, low stickiness and a balanced conditioning effect. Furthermore, a styling agent should be able to be used as universally as possible for all hair types. If the styling agent is a gel or a paste, the polymers should also have thickening properties.

The special requirements placed on styling agents are the general hold of the hairstyle and, in the case of curly hair, the degree of curl retention. In this case, "curl retention" is a measure of the degree of curl retention. The curl retention typically worsens if the treated hair is in a humid environment since the tendency of the hair to absorb moisture, i.e. water, causes the strands of hair to hang down limply.

Therefore, the object of the present invention was to provide styling compositions that bring about considerably better curl retention, in particular considerably improved high humidity curl retention, i.e. a better degree of curl retention even in humid environments, preferably whilst further improving the hold and the feel of the hair, e.g. making the hair more pleasant to the touch and easier to comb.

These objects were solved by a specific combination of polymer(s) and particular esters.

Furthermore, other desirable features and characteristics of the present invention will become apparent from the subsequent detailed description of the invention and the appended claims, taken in conjunction with this background of the invention.

BRIEF SUMMARY OF THE INVENTION

A styling agent comprising, based on its weight, from 0.1 to 20 wt. % of stabilizing polymer(s), and from 0.1 to 5 wt. % of esters of the formula (I),

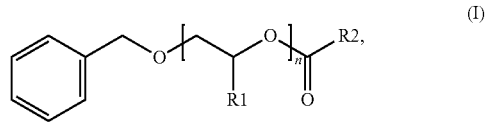

in which R1 represents —H or —CH$_3$, R2 represents a straight-chained or branched alkyl functional group having 7 to 15 carbon atoms, and n represents an integer from the group of 1, 2, 3, 4, 5, 6, 7 and 8.

The use of esters of the formula (I),

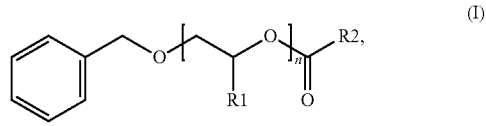

in which R1 represents —H or —CH$_3$, R2 represents a straight-chain or branched alkyl functional group having 7 to 15 carbon atoms, and n represents an integer from the group of 1, 2, 3, 4, 5, 6, 7 and 8, for improving curl retention, in particular high humidity curl retention.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The invention first relates to a styling agent comprising, based on its weight,
   a) from 0.1 to 20 wt. % of stabilizing polymer(s),
   b) from 0.1 to 5 wt. % of esters of the formula (I)

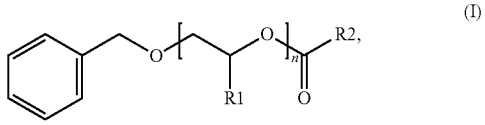

in which
R1 represents —H or —CH$_3$,
R2 represents a straight-chained or branched alkyl functional group having 7 to 15 carbon atoms,
n represents an integer from the group of 1, 2, 3, 4, 5, 6, 7 and 8.

As a first essential constituent, the styling agents according to the invention include from 0.1 to 20 wt. % of at least one stabilizing polymer.

These film-forming and/or stabilizing polymers can be both permanently and temporarily cationic, anionic, non-ionic or amphoteric. Furthermore, the present invention also includes the knowledge that when at least two film-forming and/or stabilizing polymers are used, they may of course have different charges. According to the invention, it may be preferable for an ionic film-forming and/or stabilizing polymer to be used together with an amphoteric and/or non-ionic film-forming and/or stabilizing polymer. The use of at least two film-forming and/or stabilizing polymers having opposite charges is also preferred. In the latter case, one particular embodiment can in turn also include at least one additional amphoteric and/or non-ionic film-forming and/or stabilizing polymer.

Since polymers are often multi-functional, it may not always be possible to differentiate between the functions thereof in a clear and distinct manner. This is the case in particular with film-forming and stabilizing polymers. Nevertheless, some film-forming polymers are to be described by way of example. At this juncture, however, it is explicitly pointed out that both film-forming and stabilizing polymers are essential in the context of the present invention. Since the two properties cannot be fully distinguished from one another either, "stabilizing polymers" are also always taken to mean "film-forming polymers", and vice versa.

Film formation is one of the preferred properties of the film-forming polymers. Film-forming polymers are understood to be those polymers which leave behind a continuous film on the skin, hair or nails upon drying. Film formers of this kind can be used in a wide variety of cosmetic products, such as face masks, make-up, hair stabilizers, hairsprays, hair gels, hair waxes, hair masques, shampoos or nail polishes. Polymers that are sufficiently soluble in alcohol or water/alcohol mixtures in order to be present in the agent according to the invention in a completely dissolved form are preferred in particular. The film-forming polymers can be of synthetic or natural origin.

According to the invention, film-forming polymers are also understood to be those polymers which, when used in 0.01 to 20 wt. % aqueous, alcoholic or aqueous-alcoholic solution, are capable of depositing a transparent polymer film on the hair. In this case, the film-forming polymers can be charged in an anionic, amphoteric, non-ionic, permanently cationic or temporarily cationic manner.

Suitable synthetic, film-forming, hair-stabilizing polymers are homopolymers or copolymers constructed from at least one of the following monomers: vinylpyrrolidone, vinylcaprolactam, vinyl esters such as vinyl acetate, vinyl alcohol, acrylamide, methacrylamide, alkyl and dialkyl acrylamide, alkyl acrylate, alkyl methacrylate, propylene glycol or ethylene glycol, the alkyl groups of these monomers preferably being C1 to C7 alkyl groups, particularly preferably C1 to C3 alkyl groups.

Homopolymers of vinylcaprolactam, of vinylpyrrolidone or of N-vinylformamide are mentioned by way of example. Other suitable synthetic, film-forming, hair-stabilizing polymers are, for example, copolymerisates of vinylpyrrolidone and vinyl acetate, terpolymers of vinylpyrrolidone, vinyl acetate and vinyl propionate, polyacrylamides marketed for example by CHEM-Y, Emmerich, under the trade name Akypomine® P 191, or by Seppic under the trade name Sepigel® 305; polyvinyl alcohols marketed for example by Du Pont under the trade name Elvanol® or by Air Products under the trade name Vinol® 523/540, and polyethylene glycol/polypropylene glycol copolymers marketed for example by Union Carbide under the trade name Ucon®.

Examples of suitable natural film-forming polymers are cellulose derivatives, e.g. hydroxypropyl cellulose having a molecular weight of from 30 000 to 50 000 g/mol, marketed for example by Lehmann & Voss, Hamburg, under the trade name Nisso SI®.

Stabilizing polymers contribute to the hold and/or the generation of the hair volume and the fullness of the overall hairstyle. At the same time, these stabilizing polymers are also film-forming polymers and are therefore generally typical substances for hair treatment agents that provide shaping, such as hair stabilizers, hair mousse, hair waxes and hairsprays. In the process, the films can also be formed at specific points and only connect some fibers.

Substances that also provide the hair with hydrophobic properties are preferred in this case because they reduce the tendency of the hair to absorb moisture, i.e. water. As a result, the strands of hair hang down limply to a lesser extent and thus a long-lasting hairstyle is created and retained. The curl retention test is often used as a test method for this. Said polymer substances can also be successfully included in leave-on and rinse-off hair masques or shampoos. Since polymers are often multi-functional, i.e. exhibit several effects desired for the application, there are numerous polymers in multiple groups divided up according to the action thereof, as in the CTFA handbook. Owing to the importance in particular of the stabilizing polymers, these will therefore be explicitly listed in their INCI name form. This list of the polymers to preferably be used according to the invention thus also naturally includes the aforementioned film-forming polymers.

Examples of common film-forming, stabilizing polymers are acrylamide/ammonium acrylate copolymer, acrylamide/DMAPA Acrylate/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/C1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates-VA copolymer, acrylates-VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, amino ethyl propanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetone-acrylamide copolymer, AMP-acrylates/dimethylaminoethylmethacrylate copolymer, *Bacillus*/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-45, polyquaternium-46, polyquaternium-47, polyquaternium-48, polyquaternium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilyl-carbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/DMAPA acrylates copolymer, yeast palmitate.

The hold of the hairstyle can be improved quite significantly when a film-forming and/or stabilizing polymer that forms brittle, hard polymer films is used. Preferably, therefore, appropriate film-forming and/or stabilizing polymers are used.

Therefore, the agent according to the invention preferably includes at least one film-forming and/or stabilizing polymer selected from:
- aminomethyl propanol salts of copolymers of allyl methacrylate having one or more monomers selected from acrylic acid, methacrylic acid, acrylic acid ester and methacrylic acid ester,
- vinylpyrrolidone-vinyl acetate copolymers,
- vinylpyrrolidone-vinylcaprolactam-dimethylaminopropyl acrylamide copolymers,
- copolymers of octylacrylamide having t-butylaminoethyl methacrylate and two or more monomers selected from acrylic acid, methacrylic acid, acrylic acid ester and methacrylic acid ester, and
- copolymers of $C_{1-2}$-alkyl succinates having hydroxyalkyl acrylates and one or more monomers selected from acrylic acid, methacrylic acid, acrylic acid ester and methacrylic acid ester.

Appropriate film-forming and/or stabilizing polymers are commercially available.

Particularly preferably, the agent according to the invention includes, as the film-forming and/or stabilizing polymer, an aminomethyl propanol salt of a copolymer of allyl methacrylate having one or more monomers selected from acrylic acid, methacrylic acid, acrylic acid ester and methacrylic acid ester.

Preferably, the aforementioned acrylic acid esters and methacrylic acid esters are acrylates and $C_1$-$C_{12}$-alkyl methacrylates, particularly preferably methyl acrylate, ethyl acrylate, propyl acrylate, methyl methacrylate, ethyl methacrylate, propyl methacrylate and mixtures thereof.

The copolymer with the INCI name AMP-acrylates/allyl methacrylate copolymer, marketed by Noveon under the name Fixate™ G-100, is preferably used as the aminomethyl propanol salt of copolymers of allyl methacrylate having one or more monomers selected from acrylic acid, methacrylic acid, acrylic acid ester and methacrylic acid ester. Most preferably, the agent according to the invention includes this copolymer.

PVP/VA copolymer 60-40 W (INCI name: VP/VA copolymer, aqua, laurtrimonium chloride) is a preferred vinylpyrrolidone-vinyl acetate copolymer.

The copolymer with the INCI name VP/vinylcaprolactam/DMAPA acrylates copolymer, which can be obtained from ISP under the name Aquaflex SF 40, is preferably used as the vinylpyrrolidone-vinylcaprolactam/dimethylaminopropyl acrylamide copolymer.

The copolymer with the INCI name octylacrylamide/acrylates butylaminoethyl methacrylates copolymer, which can be obtained from National Starch under the name Amphomer®, is a preferred copolymer of octylacrylamide having t-butylaminoethyl methacrylate and two or more monomers selected from acrylic acid, methacrylic acid, acrylic acid ester and methacrylic acid ester.

The copolymer with the INCI name acrylates/C1-2 succinates/hydroxyacrylates copolymer, which can be obtained from ISP under the name Allianz™ LT 120, is preferred as the copolymer of $C_{1-2}$-alkyl succinates having hydroxyalkyl acrylates and one or more monomers selected from acrylic acid, methacrylic acid, acrylic acid ester and methacrylic acid ester.

Agents which are particularly preferred according to the invention are characterized in that they include the stabilizing polymers in a total amount of from 0.2 wt. % to 17.5 wt. %, preferably from 0.5 wt. % to 15 wt. %, particularly preferably from 2.0 wt. % to 10.0 wt. %, and in particular from 3.0 to 8.0 wt. %, based on the weight of the agent in each case.

Most preferable agents according to the invention are characterized in that they include at least one stabilizing polymer selected from
  non-ionic polymers based on ethylenically unsaturated monomers, in particular from
  homopolymers of N-vinylpyrrolidone,
  non-ionic copolymers of N-vinylpyrrolidone,
  homopolymers and non-ionic copolymers of N-vinylcaprolactam,
  copolymers of (meth)acrylamide,
  polyvinyl alcohol, polyvinyl acetate,
  chitosan and chitosan derivatives,
  cationic cellulose derivatives,
  cationic copolymers of 3-(C1 to C6)-alkyl-1-vinyl-imidazolinium,
  homopolymers and copolymers having the structural unit of the formula (M-1),

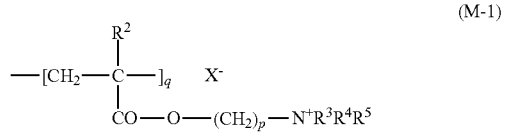

(M-1)

in which $R^2$ is —H or —$CH_3$, $R^3$, $R^4$ and $R^5$ are selected independently of one another from ($C_1$-$C_4$)-alkyl-, ($C_1$ to $C_4$)-alkenyl- or ($C_2$ to $C_4$)-hydroxyalkyl groups, p=1, 2, 3 or 4, q is a natural number and $X^-$ is a physiologically acceptable organic or inorganic anion,
  anionic polymers comprising carboxylate and/or sulfonate groups,
  anionic polyurethanes.

It has been found that a particular copolymer in the combination according to the invention provides an exceptionally good degree of curl retention, which is not only reinforced by the use of the esters described below, but are also complemented by the hair feeling pleasant to the touch. Agents preferred according to the invention are therefore characterized in that they include, based on their weight, from 0.1 to 10 wt. %, preferably from 0.25 to 9 wt. %, more preferably from 0.5 to 8 wt. %, particularly preferably from 0.75 to 7 wt. %, and in particular from 1 to 6 wt. % of copolymer(s) of N-octylacrylamide/acrylic acid/tert.-butyl amino ethyl methacrylate (INCI-name: octylacrylamide/acrylates/butylaminoethyl methacrylate copolymer).

As a second essential constituent, the agents according to the invention include from 0.01 to 5 wt. % of esters of the formula (I),

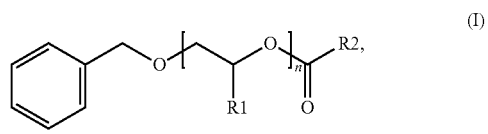

(I)

in which
R1 represents —H or —$CH_3$,
R2 represents a straight-chain or branched alkyl functional group having 7 to 15 carbon atoms,
n represents an integer from the group of 1, 2, 3, 4, 5, 6, 7 and 8.

Preferably, the ester(s) of the formula (I) is/are used within narrow volume ranges. Preferred agents are characterized in that they include, based on their weight, from 0.11 to 4.5 wt. %, preferably from 0.12 to 4 wt. %, more preferably from 0.13 to 3 wt. %, particularly preferably from 0.14 to 2.5 wt. %, and in particular from 0.15 to 2 wt. % of esters of the formula (I).

In formula (I), R1 preferably represents a methyl group, and so preferred agents are characterized in that they include, based on their weight, from 0.11 to 4.5 wt. %, preferably from 0.12 to 4 wt. %, more preferably from 0.13 to 3 wt. %, particularly preferably from 0.14 to 2.5 wt. %, and in particular from 0.15 to 2 wt. % of esters of the formula (Ia),

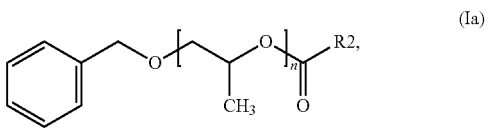

(Ia)

in which
R2 represents a straight-chain or branched alkyl functional group having 7 to 15 carbon atoms,
n represents an integer from the group of 1, 2, 3, 4, 5, 6, 7 and 8.

In formula (Ia), n preferably represents an integer from the group of 1, 2, 3, 4, 5, 6, i.e. preferred esters can be described by the formulae (Ia-1) to (Ia-6):

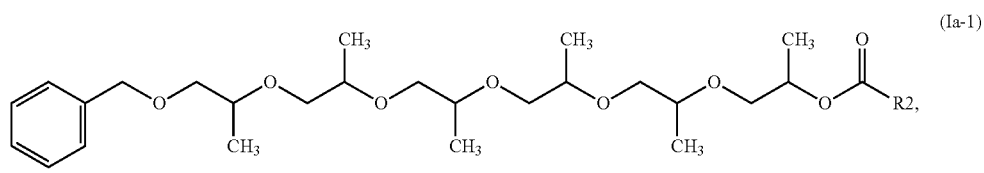
(Ia-1)

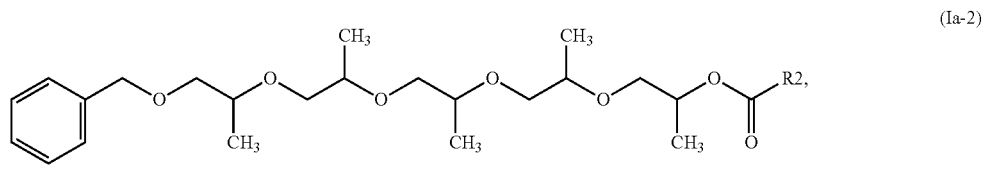
(Ia-2)

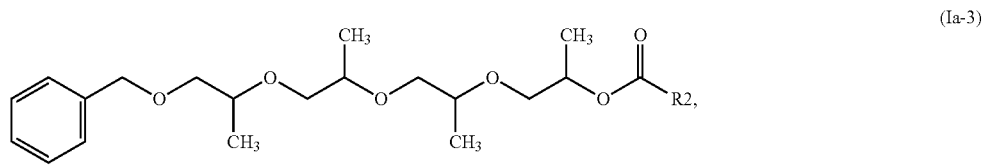
(Ia-3)

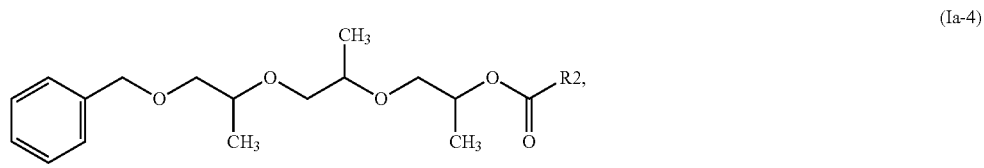
(Ia-4)

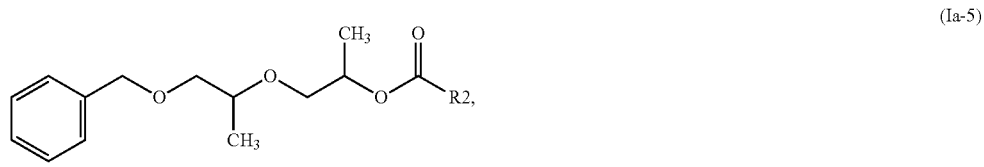
(Ia-5)

(Ia-6)

in which R2 represents in each case a straight-chain or branched alkyl functional group having 7 to 15 carbon atoms.

Most preferable functional groups R2 represent tridecyl or ethylhexyl functional groups, and so particularly preferred agents are characterized in they include, based on their weight, from 0.11 to 4.5 wt. %, preferably from 0.12 to 4 wt. %, more preferably from 0.13 to 3 wt. %, particularly preferably from 0.14 to 2.5 wt. %, and in particular from 0.15 to 2 wt. % of esters of the formula (Ib), in which n represents an integer from the group of 1, 2, 3 or 4, preferably represents 2 or 3, and in particular represents 3, and other agents that are likewise particularly preferred are characterized in that they include, based on their weight, from 0.11 to 4.5 wt. %, preferably from 0.12 to 4 wt. %, more preferably from 0.13 to 3 wt. %, particularly preferably from 0.14 to 2.5 wt. %, and in particular from 0.15 to 2 wt. % of esters of the formula (Ic)

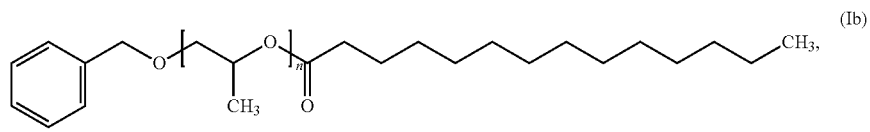
(Ib)

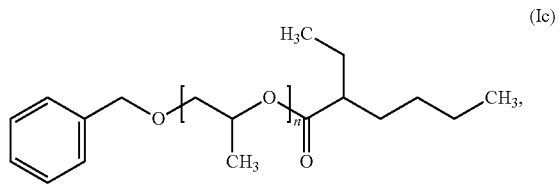

in which n represents an integer from the group of 1, 2, 3 or 4, preferably represents 2 or 3, and in particular represents 3.

Therefore esters to be most preferably used are the compounds (Ib-1) and (Ic-1):

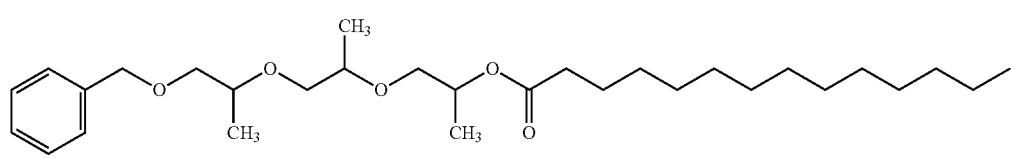

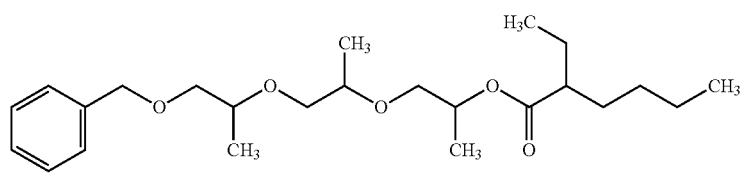

In addition to the copolymers and esters described above, the cosmetic agents according to the invention can also include additional ingredients. This group of additional ingredients includes in particular the cosmetically active auxiliary substances and additives.

As a preferred constituent, the cosmetic agents according to the invention include at least one quaternary ammonium compound. Monomeric or polymeric active ingredients can be used as the quaternary ammonium compound.

Out of the large number of possible monomeric quaternary ammonium compounds, the compounds from the groups:

trimethylalkyl ammonium halides;
esterquats
quaternary imidazoline have proven particularly effective.

The group of trimethylalkyl ammonium halides in particular includes the compounds of the formula (Tkat1-1).

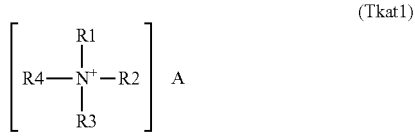

In the formula (TKat1), R1, R2, R3 and R4 each independently represent hydrogen, a methyl group, a phenyl group, a benzyl group, a saturated, branched or unbranched alkyl functional group having a chain length of 8 to 30 carbon atoms, which can possibly be substituted by one or more hydroxy groups. A represents a physiologically acceptable anion, for example halides such as chloride or bromide and methosulfates.

Examples for compounds of the formula (Tkat1) are lauryl trimethyl ammonium chloride, cetyl trimethyl ammonium chloride, cetyl trimethyl ammonium bromide, cetyl trimethyl ammonium methosulfate, dicetyl dimethyl ammonium chloride, tricetyl methyl ammonium chloride, stearyl trimethyl ammonium chloride, distearyl dimethyl ammonium chloride, lauryl dimethyl benzyl ammonium chloride, behenyl trimethyl ammonium chloride, behenyl trimethyl ammonium bromide, behenyl trimethyl ammonium methosulfate. Preferred cosmetic agents include a monomeric quaternary ammonium compound from the group of trimethyl alkyl ammonium halides.

Additional quaternary ammonium compounds that are particularly preferred according to the invention are cationic betaine esters of the formula (Tkat1-2.1).

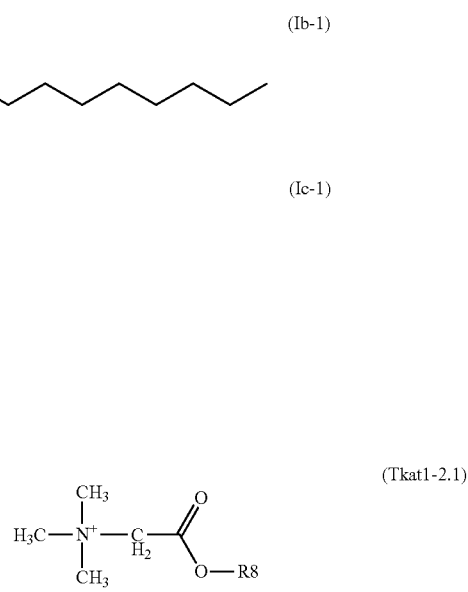

Particularly preferred are the esterquats having the trade name Armocare® VGH-70, and Dehyquart® F-75, Dehyquart® L80, Stepantex® VS 90 and Akypoquat® 131.

Another group are quaternary imidazoline compounds. The formula (Tkat2) illustrated below shows the structure of said compounds.

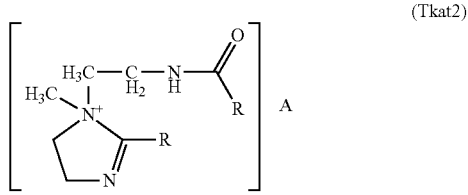

The functional groups R independently represent a saturated or unsaturated, linear or branched hydrocarbon functional group having a chain length of 8 to 30 carbon atoms. The preferred compounds of the formula (Tkat2) each include the same hydrocarbon functional group for R. The chain length of the functional groups R is preferably 12 to 21 carbon atoms. A represents an anion as described above. Examples that are particularly according to the invention can, for example, be obtained under the INCI names quaternium-27, quaternium-72, quaternium-83, quaternium-87 and quaternium-91. Quaternium-91 is the most preferred according to the invention.

In terms of the cosmetic action, cosmetic agents in which the weight fraction of the monomeric quaternary ammonium compound is from 0.05 to 3.0 wt. %, preferably from 0.1 to 2.0 wt. %, and in particular from 0.2 to 1.0 wt. % based on the total weight of the agent, have proven advantageous.

Mention should be made in particular of additional nourishing agents as suitable auxiliary agents and additives.

As a nourishing substance of another class of compounds, the agent can, for example, include at least one protein hydrolyzate and/or a derivative thereof. Protein hydrolyzates are product mixtures that are obtained by breaking down proteins in a manner catalyzed by acids, bases or enzymes. According to the invention, the term protein hydrolyzates is also understood to mean total hydrolyzates, individual amino acids and the derivatives thereof, and mixtures of various amino acids. The molar weight of the protein hydrolyzates that can be used according to the invention is between 75, the molar weight of glycine, and 200000; preferably, the molar weight is from 75 to 50000 and most preferably from 75 to 20000 Dalton.

The agent according to the invention can include at least a vitamin, a provitamin, a vitamin precursor and/or a derivative thereof as a nourishing substance. In this case, those vitamins, provitamins, and vitamin precursors that are typically assigned to the groups A, B, C, E, F and H are preferred according to the invention.

Like the admixture of glycerol and/or propylene glycol, the admixture of panthenol also increases the flexibility of the polymer film formed when the agent according to the invention is applied.

The agents according to the invention can also comprise at least one plant extract, as well as mono- or oligosaccharides and/or lipids as the nourishing substance.

Oil components are also suitable as nourishing substances. Natural and synthetic cosmetic oil components include, for example, plant oils, liquid paraffin oils, isoparaffin oils, synthetic hydrocarbons and Di-n-alkyl ethers having overall between 12 and 36 C atoms, in particular between 12 and 24 C atoms. Preferred cosmetic agents according to the invention include at least one oil component, preferably at least one oil component from the group of silicone oils. The group of silicone oils in particular includes dimethicones, which also cover cyclomethicones, amino-functional silicones and dimethiconols. The dimethicones can be linear and branched, and cyclic or cyclic and branched. Suitable silicone oils or silicone gums are in particular dialkyl and alkyl aryl siloxanes, such as dimethyl polysiloxane and methyl phenyl polysiloxane, and alkoxylated, quaternated and anionic derivatives thereof. Cyclic and linear polydialkyl siloxanes, the alkoxylated and/or aminated derivatives thereof, dihydroxy polydimethylsiloxanes and polyphenylalkyl siloxanes are preferred.

Ester oils, i.e. esters of $C_6$-$C_{30}$ fatty acids having $C_2$-$C_{30}$ fatty alcohols, preferably monoesters of fatty acids with alcohols having 2 to 24 C atoms, such as isopropyl myristate (Rilanit® IPM), isononanoic acid-C16-18-alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut oil alcohol-caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V), are other preferred nourishing oil components.

Dicarboxylic acid esters, symmetric, asymmetric or cyclic esters of carboxylic acid having fatty alcohol, tri-fatty acid esters of saturated and/or unsaturated linear and/or branched fatty acids having glycerol or fatty acid partial glycerols, which is taken to include monoglycerols, diglycerols and the technical mixtures thereof, are suitable as nourishing substances.

In terms of the cosmetic action, cosmetic agents in which the weight fraction of the oil component is from 0.01 to 5.0 wt. %, preferably from 0.02 to 4.0 wt. %, and in particular from 0.05 to 2.0 wt. % based on the total weight of the agent, have proven advantageous.

The agents according to the invention are used to temporarily shape the hair. Temporary shaping which should create good hold without affecting the healthy appearance of the hair, e.g. the shine thereof, can for example be achieved using hairsprays, hair waxes, hair gels, blow drying, etc.

In a particularly preferred embodiment of the present invention, the agent according to the invention can be designed as a hairspray. The present invention therefore also relates to an aerosol assembly, comprising a pressurized container and therein:—
a) an agent according to the invention;
b) a propellant or propellant mixture, selected from dimethyl ether, HFO1234yf, HFO1234ze, propane, propene, n-butane, iso-butane, iso-butene, n-pentane, pentene, iso-pentane, iso-pentene or mixtures thereof Propellants (propellant gases) suitable according to the invention are, for example, propane, n-butane, iso-butane, dimethyl ether (DME), nitrogen, air, nitrous oxide, 1,1-difluoroethane, and specifically both alone and in combination. Hydrophilic propellants such as carbon dioxide can also be used advantageously within the scope of the present invention if the proportion of hydrophilic gases is selected to be low and there is an excess of lipophilic propellants (e.g. propane/butane). Dimethyl ether, propane, n-butane, iso-butane and mixtures of these propellants are particularly preferred. The use of propane/butane mixtures or isobutane is most preferred.

Particularly preferred hairsprays according to the invention are characterized in that the aerosol composition includes, based on its weight, from 20 to 80 wt. %, preferably from 22.5 to 77.5 wt. %, more preferably from 25 to 75 wt. %, even more preferably from 27.5 to 72.5 wt. %, and in particular from 30 to 70 wt. % of propellant or propellant mixture selected from dimethyl ether, HFO1234yf, HFO1234ze, propane, propene, n-butane, iso-butane, iso-butene, n-pentane, pentene, iso-pentane and iso-pentene, or mixtures thereof Advantageously, the propellant is selected such that it can simultaneously act as a solvent for other ingredients, such as oil and wax components, the fatty substances (D). The propellant can be used as a solvent for these last-mentioned components if they can dissolve therein at 20° C. to at least 0.5 wt. % based on the propellant.

According to a preferred embodiment, the preparations according to the invention include the aforementioned hydrocarbons, dimethyl ether or mixtures of said hydrocarbons with dimethyl ether as one propellant. However, the invention also explicitly includes the use of propellants of the chlorofluorocarbon type, in particular fluorocarbons.

Most preferable combinations according to the invention are characterized in that the propellant-containing hair treatment agent includes, based on its weight, from 7.5 to 57.5 wt. %, preferably from 10 to 55 wt. %, more preferably from 15 to 52 wt. %, even more preferably from 17.5 to 55 wt. %, particularly preferably from 20 to 50 wt. %, and in particular from 25 to 45 wt. % of at least one propellant selected from n-propane, n-butane, iso-butane, n-pentane, dimethyl ether and mixtures thereof The combination according to the invention also includes a dispenser (pressurized container) out of which the propellant-containing hair treatment agent contained therein is sprayed by means of the propellant. According to the invention, the dispenser preferably comprises a valve containing a valve opening that is designed as a tapered hole and the diameter of which is at most 0.4 mm. In addition, the valve preferably contains a restriction that has an inner diameter of at most 0.3 mm yet has no side hole ("gas phase hole"). Preferably, the diameter of the tapered hole is from 0.15 to 0.4 mm, preferably from 0.175 to 0.375 mm, more preferably from 0.2 to 0.35 mm, and in particular from 0.25 to 0.3 mm. Preferably, the depth of the tapered hole is also at most 0.3 mm. Preferred combinations according to the invention are further characterized in that the depth of the tapered hole is from 0.1 to 0.3 mm, preferably from 0.125 to 0.275 mm, more preferably from 0.15 to 0.25 mm, and in particular from 0.2 to 0.25 mm.

The design of the valve also preferably contains a restriction that defines the flow rate. In this case, the restriction is located in either the valve stem or the spray head. In preferred embodiments of the present invention, this restriction has an inner diameter of from 0.1 to 0.3 mm, preferably from 0.125 to 0.275 mm, more preferably from 0.15 to 0.25 mm, and in particular from 0.2 to 0.25 mm.

The compositions according to the invention can be packaged in commercially available aerosol cans. The cans can be made of tin plate or aluminum. Furthermore, the cans can be coated on the inside to keep the risk of corrosion as low as possible. Inner bags can also be used in the cans without difficulty.

The cans are equipped with a suitable spray head. Depending on the spray head, expulsion rates of from 0.1 g/s to 5.0 g/s are possible, based on completely full cans.

The present invention also relates to the use of esters of the formula (I)

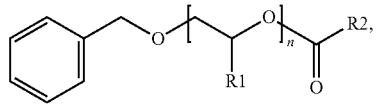
(I)

in der
in which
R1 represents —H or —CH$_3$,
R2 represents a straight-chain or branched alkyl functional group having 7 to 15 carbon atoms,
n represents an integer from the group 1, 2, 3, 4, 5, 6, 7 and 8,
for improving curl retention, in particular high humidity curl retention.

Preferred uses according to the invention use the esters in combination with at least one stabilizing polymer. The statements in relation to the agents according to the invention also apply, mutatis mutandis, in relation to other preferred embodiments of the use according to the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:
1. A styling agent, comprising, based on its weight,
a) from 0.1 to 20 wt. % of stabilizing polymer(s),
b) from 0.1 to 5 wt. % of esters of the formula (I),

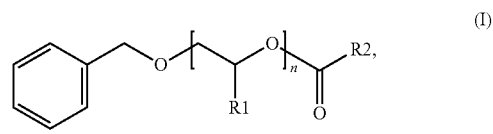
(I)

in which
R1 represents —H or —CH$_3$,
R2 represents a straight-chained or branched alkyl functional group having 7 to 15 carbon atoms, n represents an integer selected from the group of 1, 2, 3, 4, 5, 6, 7 and 8
wherein the ester of formula (I) includes a compound

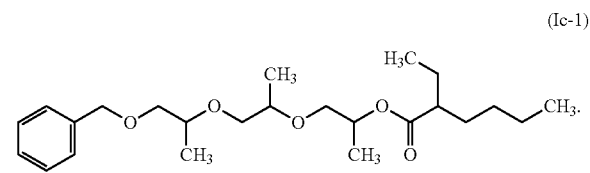 [SMILES: CCCCC(CC)C(=O)OC(C)COC(C)COC(C)COCc1ccccc1]
(Ic-1)

2. The agent according to claim 1, wherein the esters of formula (I) comprises 0.11 to 4.5 wt. % of the agent.
3. The agent according to claim 1, wherein the esters of formula (I) comprises 0.14 to 2.5 wt. % of the agent.
4. The agent according to claim 1, wherein the stabilizing polymers comprise 0.2 wt. % to 17.5 wt. % of the agent.
5. The agent according to claim 1, wherein the stabilizing polymers comprise 0.5 wt. % to 15 wt. % of the agent.
6. The agent according to claim 1, wherein the stabilizing polymers comprise, 2.0 wt. % to 10.0 wt. %.
7. The agent according to claim 1, wherein the stabilizing polymer is selected from the group consisting of:
non-ionic polymers based on ethylenically unsaturated monomers, in particular from
homopolymers of N-vinylpyrrolidone,
non-ionic copolymers of N-vinylpyrrolidone,
homopolymers and non-ionic copolymers of N-vinylcaprolactam,
copolymers of (meth)acrylamide,
polyvinyl alcohol, polyvinyl acetate,
chitosan and chitosan derivatives,
cationic cellulose derivatives,
cationic copolymers of 3-(C1 to C6)-alkyl-1-vinyl-imidazolinium,
homopolymers and copolymers having the structural unit of the formula (M-1),

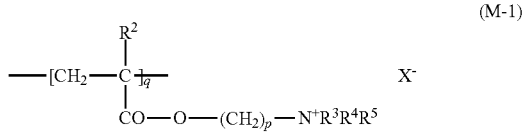 (M-1)

in which $R^2$ is —H or —$CH_3$, $R^3$, $R^4$ and $R^5$ are selected independently of one another from ($C_1$-$C_4$)-alkyl-, ($C_1$ to $C_4$)-alkenyl- or ($C_2$ to $C_4$)-hydroxyalkyl groups, p=1, 2, 3 or 4, q is a natural number and $X^-$ is a physiologically acceptable organic or inorganic anion, anionic polymers comprising carboxylate and/or sulfonate groups, and anionic polyurethanes.

8. The agent according to claim 1, wherein the stabilizing polymer comprises 0.25 to 9 wt % of the agent and includes the copolymer(s) of N-octylacrylamide/acrylic acid/tert.-butylaminoethyl methacrylate (INCI name: octylacrylamide/acrylates/butylaminoethyl methacrylate copolymer).

9. The agent according to claim 1, wherein the stabilizing polymer comprises 0.5 to 8 wt. % of the agent and includes the copolymer(s) of N-octylacrylamide/acrylic acid/tert.-butylaminoethyl methacrylate (INCI name: octylacrylamide/acrylates/butylaminoethyl methacrylate copolymer).

10. An aerosol assembly, comprising a pressurized container and therein:
a) an agent according to claim 1;
b) a propellant or propellant mixture, selected from dimethyl ether, HFO1234yf, HFO1234ze, propane, propene, n-butane, iso-butane, iso-butene, n-pentane, pentene, iso-pentane and iso-pentene or mixtures thereof.

11. The aerosol assembly according to claim 10, wherein the propellant-containing hair treatment agent comprises, based on its weight, from 7.5 to 57.5 wt. % of at least one propellant selected from the group consisting of n-propane, n-butane, iso-butane, n-pentane, dimethyl ether, and mixtures thereof.

12. The aerosol assembly according to claim 10, wherein the propellant-containing hair treatment agent comprises, based on its weight, from 15 to 52.5 wt. %of at least one propellant selected from the group consisting of n-propane, n-butane, iso-butane, n-pentane, dimethyl ether, and mixtures thereof.

* * * * *